United States Patent [19]
Regen

[11] Patent Number: 4,808,480
[45] Date of Patent: Feb. 28, 1989

[54] POLYMERIZABLE HETEROCYCLIC DISULFIDE-BASED COMPOUNDS AND MEMBRANES MADE THEREFROM

[75] Inventor: Steven L. Regen, Allentown, Pa.

[73] Assignee: Lehigh University, Bethlehem, Pa.

[21] Appl. No.: 934,766

[22] Filed: Nov. 25, 1986

[51] Int. Cl.$^4$ .................. A61K 9/66; B01J 13/02; C07D 339/02

[52] U.S. Cl. .................. 428/402.2; 264/4.3; 264/4.6; 264/4.7; 260/399; 260/402.5; 424/450; 436/829; 549/7

[58] Field of Search .............. 428/402.2; 424/450; 436/829; 260/403, 399, 402.5; 549/7

[56] References Cited

U.S. PATENT DOCUMENTS

| | | | |
|---|---|---|---|
| 4,348,329 | 9/1982 | Chapman | 260/403 |
| 4,429,008 | 1/1984 | Martin et al. | 424/450 X |
| 4,485,045 | 11/1984 | Regen | 264/4.7 X |
| 4,492,659 | 1/1985 | Bosies et al. | 558/169 |
| 4,515,736 | 5/1985 | Deamer | 264/4.3 |
| 4,594,193 | 6/1986 | Regen | 260/402.5 X |

OTHER PUBLICATIONS

Regen et al.: "Polymerization of Macrocyclic Phospholipid- and Surfactant-Based Vesicles", J. Am. Chem. Soc., 1985, 107, 5804–5805.

Primary Examiner—Richard D. Lovering
Attorney, Agent, or Firm—Ratner & Prestia

[57] ABSTRACT

Compounds adapted to making polymerizable, cross linkable vesicles and methods for making these compounds comprising combining a phophatidylcholine derivative with an acid anhydride of a heterocyclic carbon/disulfide to form reaction products which when dispersed in aqueous buffer form vesicles that are readily polymerized by the addition of a reducing agent. The reduced vesicles form polymerized, highly cross-linked, vesicles which have a much greater stability and longer shelf life.

13 Claims, No Drawings

POLYMERIZABLE HETEROCYCLIC DISULFIDE-BASED COMPOUNDS AND MEMBRANES MADE THEREFROM

BACKGROUND OF THE INVENTION

This invention pertains to stable, preferably cross-linked, lipid bilayer vesicles and to methods of making such vesicles. Lipid bilayer vesicles are of considerable current interest as models for biomembranes, as carriers of drugs, and as devices for photochemical solar energy conversion. These particles are comprised of alternating lipid bilayer and aqueous compartments arranged in a concentric fashion.

Naturally occurring and synthetic phospholipids when dispersed in water form shell-like structures known as liposoomes. As used herein, the term "phospholipid", refers to a class of compounds also known as phosphoglycerides, of which the parent compound is a phosphoric ester of glycerol in which at least one of the other glycerol hydroxyl groups is esterified with a fatty acid. Liposomes are of particular interest because of their close structural relationship to biological membranes. However, in order to maximize their utility for biomechanistic studies (membrane modeling) and for medical applications (drug delivery), liposomes should be prepared under the mildest conditions possible, so that sensitive comembrane and entrapped components can be effectively incorporated.

Liposomes formed from monomeric lipids, such as phosphatidylcholines are of limited practical utility because they are thermodynamically and biologically unstable and the rate of leakage of entrapped drugs from them is difficult to control.

Recently, polymerized vesicles formed from polymerizable materials have been synthesized. Polymerizing the lipid material from which the vesicle is formed is a highly effective method for achieving the desired enhanced stability but these types of vesicles are often difficult to synthesize. Vesicles of this type are disclosed in U.S. Pat. No. 4,594,139 (of common inventorship herewith) in which it was shown that 1,2-bis(11-mercaptoundecanoyl)-sn-glycero-3 phosphocholine can be polymerized in vesicle form via oxidation with hydrogen peroxide and subsequently depolymerized via dithiothreitol to yield the regenerated monomer.

It has also been shown by S. Regen et. al., J. Amer. Chem. Soc. 1985, Vol 107, page 5804, et seq., that a macrocyclic disulfide analog of the above compound can be polymerized in the vesicle state through ring-opening polymerization initiated by a catalytic amount of a reducing agent such as dithiothreitol.

The synthesis methods for both of these polymerized vesicle forms are somewhat elaborate, and require protecting the reactive thiol link throughout the synthesis process.

In both of the above cases, polymerization proceeds to completion within 4 hours at 50° C. affording linear polymers having a maximum number average degree of polymerization of 28. While the polymerization methods referred to above result in improved physical shelf-life of the vesicles, they do not yield vesicles that are crosslinked and which are also highly stable against lysing agents such as sodium dodecylsulfate (SDS).

BRIEF DESCRIPTION OF THE INVENTION

This invention comprises compounds which form highly stable vesicles, potentially suitable for use as sustained release chemical carriers, and to methods of making such compounds and vesicles. These compounds are polymerizable and are based on heterocyclic carbon/disulfide-ring containing phospholipids having the following structure:

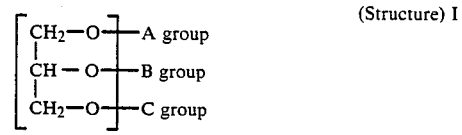

wherein one of the A, B and C groups is a head group and at least one, but preferably two, of the remaining of such A, B and C groups has the structure

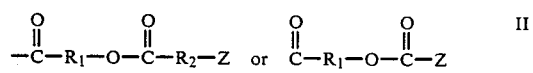

wherein $R_1$ and $R_2$ are $C_1$ to $C_{26}$ hydrocarbon radicals. Such radical may comprise linear, branched or cyclic alkyl, alkenyl, aryl, alkylaryl, or arylalkyl substituents.

Z is a heterocyclic carbon/disulfide of up to 5 carbons such as

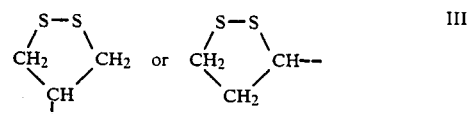

These compounds form membranes or vesicles when placed in aqueous medium, which can be transformed into highly stable, cross-linked polymeric analogs.

Also included within this invention is a process for making such compounds by esterification of the cadmium chloride complex of glycerophosphocholine (GPC-CdCl$_2$) with 12-(tetrahydropyranyloxy)-dodecanoic acid, using dicyclohexylcarbodiimide (DCC) as the condensing agent and 4-(dimethylamino)-pyridine (DMAP) as the catalyst, to produce the corresponding phosphatidylcholine. Deprotection of the corresponding phosphatidylcholine via ion exchange catalyzed methanolysis and esterification of the deprotected corresponding phosphatidylcholine with an acid anhydride of a heterocyclic carbon disulfide in the presence of an additional quantity of DMAP produces polymerizable vesicle precursors. Dispersing said vesicle precursors in an aqueous buffer and adding an agent such as dithiothreitol, produces polymerized vesicles which are highly stable against lysing agents such as sodium dodecylsulfate.

DETAILED DESCRIPTION OF THE INVENTION—PREFERRED EMBODIMENTS AND EXAMPLES

Preferably, $R_1 = C_7$ to $C_{15}$ linear or branched alkyl or alkenyl groups and $R_2 = O$ or $C_1$ to $C_4$ linear or branched alkyl or alkenyl groups.

More preferably, structure I includes two structure II substituents in which $R_1 = C_7$ to $C_{15}$ alkyls and $R_2 = O$ or $C_1$ to $C_4$ alkyls. Most preferably, $R_1 = (CH_2)_{11}$ and $R_2 = (CH_2)_4$ or O (i.e. Z is linked directly to the carbonyl and there is no intervening $R_2$ substituent).

Structure I compounds, including only one structure II substituent would include as the third group an inert group such as

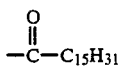

However, such compounds would not cross-link in the absence of a cross-linking agent.

The head groups (or liposome-forming) groups in the compounds and vesicles of this invention are typified by phosphatidylcholine type groups such as those having the structure

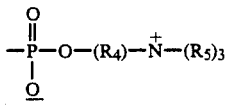

wherein $R_4$ and $R_5$ are saturated or unsaturated $C_1$ to $C_4$ hydrocarbon radicals; $R_4$ is preferably a $C_2$-$C_4$ alkyl group. $R_5$ is preferably a $C_1$-$C_2$ alkyl group.

When the structure I compounds are prepared in accordance with the present invention, they form unpolymerized compounds.

Polymerization and cross-linking of these compounds occur when the heterocyclic carbon/disulfide-containing substituents of these compounds are ring opened and then react with one another intermolecularly. This may occur spontaneously, but preferably is induced by reaction with a reducing compound, such as dithiothreitol or octanethiol. Other possible reducing agents include trialkyl phosphine in water and mercaptoethanol. Generally, the reduction is carried out at room temperature.

Generally, the structure I compounds may be formed by reacting

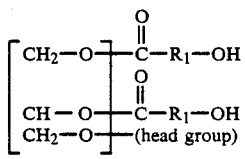

with an acid anhydride precursor of the structure II substituent group, such as

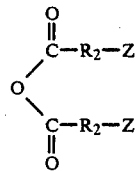

in the presence of DMAP to form

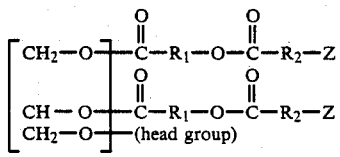

This reaction may be conducted at a temperature of about 25° C. to 40° C., under nitrogen atmosphere, at ambient pressure in dichloromethane.

Other types of head groups that might be synthesized would be derivative phospholipids such as phosphatidylalkanolamines and phosphotidylglycerols. These compounds are readily accessible through standard enzymatic exchange using phospholipase D. Pharmaceutically acceptable salts of the head groups may also be used.

Where the head group is a phosphorylcholine group, *the preferred source of the head group is sn-glycero-3-phosphorylcholine (GPC) converted as a $CdCl_2$ complex (GPC-$CdCl_2$).* For a more specific description of one method of forming the structure VIII starting material, reference is made to the detailed description of the example below.

General Procedure for Forming Vesicles

Unilamellar vesicles derived from structure I compounds have been prepared by either of two methods. In the first method the compounds, in ethanol solution, are dispersed into a 10 mM borate buffer (pH 8.5) containing 140 mM NaCl and 2 mM $NaN_3$, in which the unilamellar vesicles form spontaneously.

In the second method, the compounds, in dichloromethane solution, are deposited on the wall of a round bottom flask by evaporation of the solvent. The dried residue is dispersed in aqueous buffered solution, such as 10 mM borate (pH 8.5), containing 140 mM NaCl and 2 mM $NaN_3$, with brief vortex mixing. The resulting multilamellar vesicles are then extruded through porous membranes, such as polycarbonate filters. This procedure is described, for example, in Hope et al., Biochim. Biophys. Acta, 1985, 812,55 and Mayer et al., Biochim. Biophys. Acta, 1986, 858, 161.

The vesicles produced by the above methods have an average diameter ranging, typically, between 220 and 400 angstroms.

General Polymerization of the Vesicles Reductive Polymerization

Unlike the method of oxidative polymerization disclosed in U. S. Pat. No. 4,594,193, polymerization of the vesicles of the present invention proceeds spontaneously or preferably is accelerated in the presence of a reducing agent. The treatment of an unpolymerized vesicle dispersion of typical structure I compound with an effective amount of dithiothreitol, typically 10 mol %, results in complete polymerization of the vesicles in approximately 4 hours at 27° C.

Polymerization of the 5 member cyclic disulfide was indicated by the loss of UV absorption at 333 nM. This followed clean first order kinetics as measured by a decrease in absorbance. This polymerization was essentially complete (>95%) within 4 hours. In the absence of DTT, extensive (but incomplete) polymerization was observed after 72 hours at 23° C. or 6 hours at 50° C.

Examination of the polymerized dispersion by light scattering indicated a slight reduction in particle size; i.e., the apparent diameters ranged between 240 and 370 angstroms. Electron micrographs confirmed the presence of closed vesicles having an average diameter of 320±50 angstroms; the apparent thickness of the vesicle membrane is estimated to be 75±15 angstroms. Space filling models for structure I compounds predict a maximum lipid length of ca. 28 angstroms, when the and chains are fully extended. Thus, electron microscopy provides strong support for the expected bilayer structure. Gel filtration of these polymerized liposomes, using a Sephadex G 50 column, resulted in a 92% lipid recovery in the void volume (phosphorus analysis).

Solubility, Stability, and Permeability Properties

In contrast to liposomes comprised of low molecular weight, disulfide-based phospholipid polymers of U.S. Pat. No. 4,594,193 to Regen, freeze-dried polymerized liposomes of structure I compounds are insoluble in chloroform and chloroform/methanol (1/1 v/v). This insolubility provides stron9 indirect evidence for extensive crosslinking; i.e., each liposome is presumed to be one polymer molecule. Morever, unlike the former, which are readily lysed in 0.6% SDS, polymerized liposomes derived from structure I compounds are completely stable in 1% SDS, even after brief heating at 60° C., Nonpolymerized vesicles of structure I compounds are readily destroyed with 0.05% SDS at room temperature. Particle size analysis of the polymerized liposomal dispersion, as measured by dynamic light scattering, showed no detectable change in size distribution after 3 months of storage at room temperature. Entrapment of [$^{14}$C] sucrose within polymerized liposomes of structure I compounds, and subsequent dialysis against distilled water, using standard procedure, revealed 61% retention of the marker after 4 hours at 23° C. Under identical conditions, nonpolymerized vesicles retained 32% of the entrapped sucrose.

General Methods

Unless stated otherwise, all reagents and chemicals were obtained from commercial sources and used without further purification. House-deionized water was further purified by using a Millipore Milli-Q filtering system containing one carbon and two ion-exchange stages. sn-Glycero-3-phosphorylcholine (GPC) was freshly prepared from egg lecithin and converted into its $CdCl_2$ complex (GPC $CdCl_2$) by using established methods. [$^{14}$C] Sucrose (400 mCi/mmol, 20% ethanol solution) was obtained from ICN Laboratories. Lipoic acid (Sigma), dihydropyran (Aldrich), and dicyclohexylcarbodiimide (Aldrich) were used as obtained. 12-Hydroxydodecanoic acid (Aldrich) and 4-(dimethylamino)pyridine (DMAP, Aldrich) were recrystallized once from benzene prior to use. Tetrahydrofuran was purified by distillation over sodium benzophenone ketyl. Vesicle dispersions were prepared in 10mM borate buffer (pH 8.5) containing 140 mM NaCl and 2mM $NaN_3$. Chloroform and methanol used for chromatography were reagent grade (Aldrich). Dichloromethane (Aldrich, Gold Label) was used as obtained. IR, ($^1$H)NMR, IR, and UV spectra were recorded on Beckman Acculab 7, JEOL FX 90Q, and Bausch & Lomb Spectronic 2000 spectrometers, respectively. Chemical shifts are reported relative to tetramethylsilane. Elemental analyses were performed by Robertson Laboratory, Inc. (Florham Park, NJ). Chromatographic separations were carried out by using precoated Merck 0.25-mm silica gel 60 TLC plates (with fluorescent indicator) and Merck 70 230 ASTM silica gel with the following eluting solvents mixtures: (A) $CHCl_3/CH_3OH$ (Volume ratio 9:1); (B) $CHCl_3/CH_3OH/H_2O$ (Volume ratio 4:5:1) (C) $CHCl_3/CH_3OH/H_2O$ (Volume ratio 65:25:4). Detection on TLC plates was made by using iodine vapor or phosphomolybdic acid (10% in ethanol). Vortex mixing was carried out by using a VWR Scientific mixer (Model K-550 G). Specific procedures used for electron microscopy were similar to those previously described; 2% uranyl acetate was used as the staining agent. Electron micrographs were recorded by using a Philips 300 microscope. Freeze drying of vesicle dispersions was carried out by using a Virtis freeze dryer. Liquid scintillation was performed with a Beckman instrument, Model LS 5801, using a liquid scintillation cocktail comprised of 70% 1, 2, 4-trimethylbenzene plus 30% surfactant ("Mini Blend", ICN Laboratories). Dynamic light scattering measurements were carried out by using a Nicomp 270 submicrometer particle analyzer, equipped with a helium-neon laser (632.8 nm, scattering angle of 90°) and a computing autocorrelator. Samples were filtered by using a 0.45- m HV4 Millipore filter prior to analysis. Phosphorus analysis was performed by using established procedures.

Following is a specific example of the foregoing synthesis procedure:

Step 1

12-(Tetrahydropyranyloxy)dodecanoic Acid. 12-Hydroxydodecanoic acid (2.16 g, 10.0 mmol) was suspended in 20mL of dry THF. After the addition of 1.39g (16.5 mmol) of dihydropyran, the solution was stirred for 10 min. at room temperature. Twenty mg (0.105 mmol) of crystalline p-toluenesulfonic acid monohydrate was then added. The mixture became clear immediately, and was stirred for an additional 2 hours at room temperature. Evaporation of solvent under reduced pressure afforded a crude product which was purified by flash chromatography ($CHCl_3$) to yield 2.40 g (80%) of 12-(tetrahydropyranyloxy)dodecanoic acid as a colorless oil.

Step 2

1,2-Bis(12-hydroxydodecanoyl)-sn-glycero-3-phosphocholine (compound 2). A mixture of 3.79 g (12.6 mmol) of 12-(tetrahydropyranyloxy)dodecanoic acid, 1.381 g (3 15 mmol) of GPC-$CdCl_2$, 0.854 g (7.0 mmol) of 4-(dimethylamino)pyridine, and 1.648 g (8.0 mmol) of dicyclohexylcarbodiimide was suspended in 15mL of dry dichloromethane and stirred under nitrogen in the dark for 40 hours. After removal of solvent in vacuo, the residue was dissolved in 50 mL of methanol/water (95/5, v/v) and stirred in the presence of 8.0g of AG MP-50 (23° C.) to allow for complete deprotection of the hydroxyl groups (monitored by thin-layer chromatography). The resin was then removed by filtration and the solution concentrated under reduced pressure (at 0.05 mM Hg). The crude product (2.75 g), obtained after drying at 23° C. for 12 hours, was then subjected to chromatographic purfication by using a silica gel column with solvent mixtures A and C, to yield 0.990 g (48%) of compound 2.

Step 3

Lipoic Acid Anhydride. A mixture of lipoic acid (1.03 g, 5.0 mmol) and dicyclohexylcarbodiimide (0.65 g, 3.0 mmol) was stirred in 15 mL of dry methylene chloride for 20 hours at room temperature under a nitrogen atmosphere. The product mixture was filtered in order to remove the urea which had formed. Examination of the filtrate by IR revealed the presence of lipoic acid anhydride (1735 and 1805cm$^{-1}$) and the absence of the parent carboxylic acid ($v_{c=o}$1701 cm$^{-1}$).

This solution was used directly in the synthesis of compound 1 described below.

1,2-Bis[12-(lipoyloxy)dodecanoyl]-sn-glycero-3-phosphocholine (compound 1). 1,2-Bis(12-hydroxydodecanoyl-sn-glycero-3-phosphocholine (0.04 g, 0.06 mmol) was added to 2.0 mL of a 0.15M solution of lipoic acid containing 16 mg (0.13 mmol) of 4-(dimethylamino)pyridine. After the mixture stirred for 6 hours under nitrogen at room temperature, thin-layer chromatography (silica, solvent C) indicated complete conversion to compound 1. The product mixture was then filtered and concentrated under reduced pressure. The residue was dissolved in 5 mL of solvent mixture B and passed through a 1.2×1.5 cm AG MP-50 cation-exchange column in order to remove 4-(dimethylamino)pyridine. The filtrate was concentrated under reduced pressure, dissolved in a minimum volume of absolute ethanol, and then concentrated again. Chromatographic purification of the residue on a silica gel column (0.9×6 cm), eluting first with solvent A and then with solvent C (compound 1 elutes on silica as a single yellow band), afforded, after drying at 22° C. for 10 hours, 22° C. (at 0.05 mM Hg) 0.055 g (90%) of compound 1 as a yellow solid.

Upon drying, a small and unavoidable percentage (less than 10%) of compound 1 became polymerized on the walls of the glass flask. For storage purposes, the lipid was dissolved in dichloromethane (0.017M), filtered (0.2- m FG Millipore filter), and kept at 0° C. in the dark.

While this invention has been described with reference to specific embodiments, it is not limited thereto. The appended claims are intended to be construed to include all forms and variants of the invention as may be devised by those skilled in the art without departing from the true spirit and scope thereof.

I claim:

1. A compound of the structure

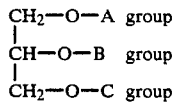

wherein one of said A, B and C groups is a liposome forming head group adapted to forming vesicles, and the remaining A, B and C groups have the structure Q wherein Q is

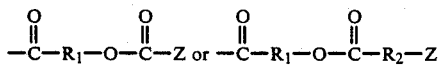

wherein $R_1$ is a hydrocarbon radical containing 1 to 26 carbons $R_2$ is a hydrocarbon radical containing 1 to 26 carbons, z is a heterocyclic carbon/disulfide.

2. A compound as in claim 1, wherein said head group has the structure:

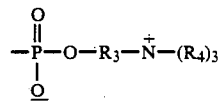

wherein $R_3$ and $R_4$ are $C_1$ to $C_4$ hydrocarbon radicals.

3. A vesicle formed from a compound of claim 2.

4. A compound as in claim 1 wherein said head group has the structure

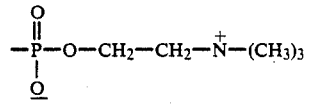

5. A compound as in claim 1 wherein said headgroup is selected from the grou consisting of posphatidylcholine, phosphatidylalkanolamine, phosphatidylglycerol and pharmaceutically acceptable salts thereof.

6. A compound as in claim 1 wherein $R_1=(CH_2)_{11}$, $R_2=(CH_2)_4$ and

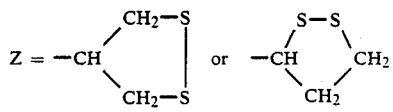

7. A vesicle formed from a compound of claim 6.

8. A compound as in claim 1 wherein $R_1=(CH_2)_{11}$, $R_2=O$ and

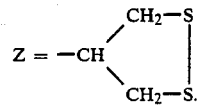

9. A vesicle formed from a compound of claim 8.

10. A compound as in claim 1 wherein $R_1=(CH_2)_{15}$, $R=(CH_2)_4$ and

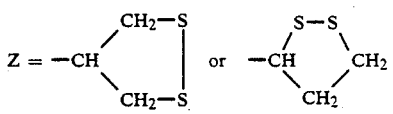

11. A vesicle formed from a compound of claim 10.

12. A vesicle formed from a compound of claim 1.

13. A compound, as recited in claim 1, wherein one of said A, B and C groups is a liposome forming heaad group adapted to form vesicles, one of said A, B and C groups has the structure Q, and the remainder of said A, B and C groups is a carbonylhydrocarbon chain.

* * * * *

UNITED STATES PATENT AND TRADEMARK OFFICE
CERTIFICATE OF CORRECTION

PATENT NO. : 4,808,480
DATED : 2/28/89
INVENTOR(S) : Steven L. Regen

It is certified that error appears in the above—identified patent and that said Letters Patent is hereby corrected as shown below:

Column 1, line 17 change "liposoomes" to --liposomes--.
Column 3, lines 35 to 43 and lines 56 to 64, the portions of the formulas in brackets should appear as:

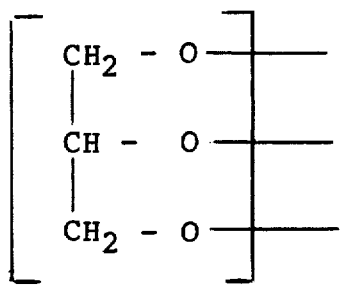

Column 5, line 8, change "stron9" to --strong--.
Column 6, line 36, change "3 15" to --3.15--.
        line 59, change "mitrogen" to --nitrogen--.

UNITED STATES PATENT AND TRADEMARK OFFICE
CERTIFICATE OF CORRECTION

PATENT NO. : 4,808,480

DATED : 2/28/89

INVENTOR(S) : Steven L. Regen

It is certified that error appears in the above-identified patent and that said Letters Patent is hereby corrected as shown below:

Column 7, line 18, delete "at 22°C".

Column 7, line 26, change "0.2 m" to --0.2 micron--.

Column 8, lines 1-5, the portion of the formula shown as "$-\overline{N}-$" should read -- $-\overset{+}{N}-$ --.

Column 8, line 18, change "grou" to --group--.

Signed and Sealed this

Twenty-eighth Day of November 1989

*Attest:*

JEFFREY M. SAMUELS

*Attesting Officer*     *Acting Commissioner of Patents and Trademarks*